United States Patent
Kleyer et al.

(10) Patent No.: US 9,045,647 B2
(45) Date of Patent: Jun. 2, 2015

(54) SURFACE TREATMENT COMPOSITION, METHOD OF PRODUCING THE SURFACE TREATMENT COMPOSITION, AND SURFACE-TREATED ARTICLE

(75) Inventors: Don Lee Kleyer, Hemlock, MI (US); Yasushi Sugiura, Ichihara (JP); Mamoru Tachikawa, Ichihara (JP); Yoshinori Taniguchi, Ichihara (JP); Peter Hupfield, Trevaughan Carmarthen (GB); Yasuo Itami, Settsu (JP); Masahiko Maeda, Osaka (JP); Tetsuya Masutani, Osaka (JP); Tomohiro Yoshida, Settsu (JP)

(73) Assignees: DOW CORNING CORPORATION, Midland, MI (US); DAIKIN INDUSTRIES, LTD., Osaka-Shi, Osaka (JP)

( * ) Notice: Subject to any disclaimer, the term of this patent is extended or adjusted under 35 U.S.C. 154(b) by 209 days.

(21) Appl. No.: 13/884,452

(22) PCT Filed: Nov. 10, 2011

(86) PCT No.: PCT/US2011/060240
§ 371 (c)(1),
(2), (4) Date: May 9, 2013

(87) PCT Pub. No.: WO2012/064989
PCT Pub. Date: May 18, 2012

(65) Prior Publication Data
US 2013/0228100 A1 Sep. 5, 2013

Related U.S. Application Data

(60) Provisional application No. 61/412,166, filed on Nov. 10, 2010.

(51) Int. Cl.
| | |
|---|---|
| *C09D 5/00* | (2006.01) |
| *C07F 7/00* | (2006.01) |
| *C07F 7/14* | (2006.01) |
| *C07F 7/18* | (2006.01) |
| *C09D 4/00* | (2006.01) |
| *C08G 65/00* | (2006.01) |
| *C08G 65/336* | (2006.01) |
| *C09D 171/02* | (2006.01) |

(52) U.S. Cl.
CPC ... *C09D 5/00* (2013.01); *C07F 7/14* (2013.01); *C07F 7/188* (2013.01); *C09D 4/00* (2013.01); *C08G 65/007* (2013.01); *C08G 65/336* (2013.01); *C09D 171/02* (2013.01); *C08G 2650/48* (2013.01)

(58) Field of Classification Search
CPC .......... C09D 4/00; C09D 5/00; C09D 171/02; C08G 65/007; C08G 65/336; C07F 7/14; C07F 7/188

USPC ...................................... 106/287.14; 556/454
See application file for complete search history.

(56) References Cited

U.S. PATENT DOCUMENTS

| | | | |
|---|---|---|---|
| 5,288,831 | A | 2/1994 | Ichinohe et al. |
| 5,986,124 | A | 11/1999 | Tachikawa et al. |
| 7,294,731 | B1 | 11/2007 | Flynn et al. |
| 8,147,954 | B2 | 4/2012 | Lee et al. |
| 8,211,544 | B2 | 7/2012 | Itami et al. |
| 2003/0139620 | A1 | 7/2003 | Yamaguchi et al. |
| 2008/0008888 | A1 | 1/2008 | Chang et al. |
| 2010/0173166 | A1 | 7/2010 | Dams et al. |

FOREIGN PATENT DOCUMENTS

| | | |
|---|---|---|
| CN | 101103083 A | 1/2008 |
| CN | 101151269 A | 3/2008 |
| CN | 101456947 A | 6/2009 |
| CN | 101501046 A | 8/2009 |
| CN | 101679572 A | 3/2010 |
| EP | 0414186 A2 | 2/1991 |
| EP | 0538061 A2 | 4/1993 |
| JP | H 02-302438 A | 12/1990 |
| JP | 2000-143679 A | 5/2000 |
| JP | 2003-238577 A | 8/2003 |
| JP | 2008-534696 A | 8/2008 |
| TW | I435900 B | 5/2014 |
| WO | WO 2006107083 A | 10/2006 |
| WO | WO 2008027697 A1 | 3/2008 |
| WO | WO 2011060047 A1 | 5/2011 |

OTHER PUBLICATIONS

English language abstract not found for TWI435900; however, see English language equivalent U.S. 8,211,544. Original document extracted from espacenet.com database on Aug. 25, 2014, 31 pages.
Brook, Michael et al., "Silicon in Organic, Organometallic, and Polymer Chemistry", John Wiley & Sons, Inc., 2000, pp. 406-407.
Yamabe, Masaaki et al., "Application of Fluoro Functional Materials", CMC Publishing Co., Ltd., Jun. 30, 2006, pp. 44-48 (with machine-assisted English translation).
English language abstract for JPH 02-302438 extracted from espacenet.com database on Oct. 27, 2014, 1 page.
English language abstract for JP 2000-143679 extracted from espacenet.com database on Oct. 27, 2014, 2 pages.
English language abstract for JP 2003-238577 extracted from espacenet.com database on Oct. 27, 2014, 2 pages.

(Continued)

*Primary Examiner* — Porfirio Nazario Gonzalez
(74) *Attorney, Agent, or Firm* — Howard & Howard Attorneys PLLC

(57) ABSTRACT

A surface treatment composition comprises a polyfluoropolyether silane. The polyfluoropolyether silane and the surface treatment composition are produced by reacting a perfluoropolyether-containing compound and a hydrosilane in the presence of a hydrosilylation catalyst and an isomer reducing agent.

17 Claims, No Drawings

(56) References Cited

OTHER PUBLICATIONS

English language abstract for JP 2008-534696 extracted from espacenet.com database on Oct. 27, 2014, 1 page.
English language abstract for CN 101103083 extracted from espacenet.com database on Nov. 26, 2014, 1 page.
Machine-assisted English translation for CN 101151269 extracted from espacenet.com database on Nov. 26, 2014, 63 pages.
English language abstract for CN 101456947 extracted from espacenet.com database on Nov. 26, 2014, 2 pages.
English language abstract for CN 101501046 extracted from espacenet.com database on Nov. 26, 2014, 1 page.
English language abstract for CN 101679572 extracted from espacenet.com database on Nov. 26, 2014, 1 page.
Zhang, Heng et al., "Synthesis and Properties of Perfluoropolyethers", Organofluorine, Periodical 1, Mar. 15, 2008, pp. 31-34, with English language abstract.
International Search Report for Application No. PCT/US2011/060240 dated Feb. 14, 2012, 4 pages.

SURFACE TREATMENT COMPOSITION, METHOD OF PRODUCING THE SURFACE TREATMENT COMPOSITION, AND SURFACE-TREATED ARTICLE

RELATED APPLICATIONS

This application is the National Stage of International Patent Application No. PCT/US2011/060240, filed on Nov. 10, 2011, which claims priority to and all the advantages of U.S. Patent Application No. 61/412,166, filed on Nov. 10, 2010, the content of which is incorporated herein by reference.

FIELD OF THE INVENTION

The present invention generally relates to a surface treatment composition. More specifically, the present invention relates to a surface treatment composition comprising a polyfluoropolyether silane, a method of producing the surface treatment composition and a surface-treated article.

DESCRIPTION OF THE RELATED ART

Electronic and optical devices/components are susceptible to staining and smudging, which is primarily attributable to contact with skin, e.g. fingers. For example, electronic devices which include an interactive touch-screen display, e.g. smart phones, are oftentimes stained and/or smudged with fingerprints, skin oil, sweat, cosmetics, etc., when used. Once these stains and/or smudges adhere to the displays of the devices, the stains and/or smudges are not easily removed. Moreover, such stains and/or smudges decrease the appearance and usability of these devices.

In an attempt to minimize the appearance and prevalence of such stains and smudges, surface treatment compositions are applied on the displays of electronic devices. However, conventional surface treatment compositions include various isomers, nonreactive components, and residual unreacted components from producing the conventional surface treatment compositions. These isomers, nonreactive components, and residual unreacted components have deleterious effects with respect to the physical properties obtained from the conventional surface treatment compositions.

SUMMARY OF THE INVENTION AND ADVANTAGES

The present invention provides a surface treatment composition comprising a polyfluoropolyether silane. The polyfluoropolyether silane of the surface treatment composition has the following general formula (A): $Y-Z_a-[(OC_3F_6)_b-(OCF(CF_3)CF_2)_c-(OCF_2CF(CF_3))_d-(OC_2F_4)_e-(CF(CF_3))_f-(OCF_2)_g]-(CH_2)_h-X-(C_nH_{2n})-((SiR_2-O)_m-SiR_2)_i-(C_jH_{2j})-Si-(X')_{3-z}(R^1)_z$.

In general formula (A), Z is independently selected from $-(CF_2)-$, $-(CF(CF_3)CF_2O)-$, $-(CF_2CF(CF_3)O)-$, $-(CF(CF_3)O)-$, $-(CF(CF_3)CF_2)-$, $-(CF_2CF(CF_3-$, and $-(CF(CF_3))-$; a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; $R^1$ is an independently selected hydrocarbon group having from 1 to 22 carbon atoms which is free of aliphatic unsaturation; and Y is selected from F and $Si-(X')_{3-z}(R^1)_z(C_jH_{2j})-((SiR_2-O)_m-SiR_2)_i-(C_nH_{2n})-X-(CH_2)_h-$; wherein X', z, $R^1$, j, m, i, n and h are as defined above.

In addition, when subscript i is 0, subscript j is also 0; when subscript i is an integer greater than 0, subscript j is also an integer greater than 0; and when subscript i is an integer greater than 0, m is also an integer greater than 0.

Furthermore, when Y is F; Z is $-(CF_2)-$; a is an integer from 1 to 3; and subscripts c, d, f and i are 0; fluorine-containing compounds represented by the general formula (B) below are present in the surface treatment composition in an amount of at least 25 mol % based on the total amount of the surface treatment composition: $F-(CF_2)_a-(OC_3F_6)_b-(OC_2F_4)_e-(OCF_2)_g-F$ (B).

In the surface treatment composition, fluorine-containing compounds represented by the general formula (C) below are present in an amount of less than 40 mol % based on the total amount of the surface treatment composition: $Y'-Z_a-[(OC_3F_6)_b-(OCF(CF_3)CF_2)_c-(OCF_2CF(CF_3))_d-OC_2F_4)_e-(CF(CF_3))_f-(OCF_2)_g]-(CH_2)_h-X-(C_nH_{2n})-CR^5=CR^5-CH_3$ (C); wherein Y' is selected from F and $CH_3-CR^5=CR^5-(C_nH_{2n})-X-(CH_2)_h-$; n' is an integer independently selected from 0 to 17; $R^5$ is independently selected from a hydrogen atom and a methyl group; and Z, a, b, c, d, e, f, g, h and X are as defined above.

The present invention also provides a method for producing the surface treatment composition. The method comprises the step of providing: a perfluoropolyether-containing compound having at least one aliphatically unsaturated group; a hydrosilane compound; a hydrosilylation catalyst; and an isomer reducing agent. The method further comprises the step of reacting the perfluoropolyether-containing compound and the hydrosilane compound in the presence of the hydrosilylation catalyst and the isomer reducing agent, thereby producing the polyfluoropolyether silane and the surface treatment composition.

The present invention further provides a surface-treated article. The surface treated article comprises an article presenting a surface. A layer is deposited on the surface of the article, and the layer is formed from the surface treatment composition.

The surface treatment composition of the present invention has excellent physical properties, including durability and resistance to staining and smudging.

DETAILED DESCRIPTION OF THE INVENTION

The present invention provides a surface treatment composition, a method of producing the surface treatment composition, and a surface-treated article. The surface treatment composition has excellent physical properties, such as stain resistance, smudge resistance, durability, and low surface tension. Thus, the surface treatment composition is particularly suitable for forming a layer on a surface presented by an article, such as an electronic article, for improving the physical properties of the article, as described in greater detail below. However, it is to be appreciated that the surface treatment composition is not limited to such uses or articles. For example, the surface treatment composition is also suitable for forming a layer on other articles and/or substrates, such as glass.

The surface treatment composition of the present invention comprises a polyfluoropolyether silane having the following general formula (A): $Y-Z_a-[(OC_3F_6)_b-(OCF(CF_3)CF_2)_c-(OCF_2CF(CF_3))_d-(OC_2F_4)_e-(CF(CF_3))_f-(OCF_2)_g]-(CH_2)_h-X-(C_nH_{2n})-((SiR_2-O)_m-$ $SiR_2)_i$—$(C_jH_{2j})$—Si—$(X')_{3-z}(R^1)_z$. It is to be appreciated that the groups represented by subscripts b-g, i.e., the groups within the square brackets in formula (A), may be present in any order within the polyfluoropolyether silane, including a different order as that which is represented in general formula (A) above and throughout this description. Moreover, these groups may be present in randomized or block form. In addition, the group represented by subscript b is typically linear, i.e., the group represented by subscript b may alternatively be written as $(O-CF_2-CF_2-CF_2)_b$.

In general formula (A) above, Z is independently selected from —$(CF_2)$—, —$(CF(CF_3)CF_2O)$—, —$(CF_2CF(CF_3)O)$—, —$(CF(CF_3)O)$—, —$(CF(CF_3)-CF_2)$—, —$(CF_2-CF(CF_3))$—, and —$(CF(CF_3))$—. In certain embodiments, Z and the moiety represented by —$[(OC_3F_6)_b$—$(OCH(CF_3)CF_2)_c$—$(OCF_2CF(CF_3))_d$—$(OC_2F_4)_e$—$(CF(CF_3))_f$—$(OCF_2)_g]$— are typically selected such that Z and this moiety do not form a peroxide. It is to be appreciated that Z is typically selected such that the polyfluoropolyether silane does not include an oxygen-oxygen (O—O) bond within the backbone. In addition, in this general formula, a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; $R^1$ is an independently selected hydrocarbon group having from 1 to 22 carbon atoms which is free of aliphatic unsaturation; and Y is selected from F and Si—$(X')_{3-z}(R^1)_z(C_jH_{2j})$—$((SiR_2-O)_m$—$SiR_2)_i$—$(C_nH_{2n})$—X—$(CH_2)_h$—; wherein X', z, $R^1$, j, m, i, n and h are as defined above.

R, which may be a hydrocarbon group having from 1 to 22 carbon atoms, may be linear, branched, or cyclic. In addition, R may include heteroatoms within the hydrocarbon group, and may be substituted or unsubstituted. In addition, the groups represented by subscripts n and j, i.e., groups $(C_nH_{2n})$ and $(C_jH_{2j})$, may also be independently linear or branched. For example, when n is 3, these groups may independently have the structure —$CH_2$—$CH_2$—$CH_2$—, —$CH(CH_3)$—$CH_2$—, or —$CH_2$—$CH(CH_3)$—, wherein the latter two structures have pendent alkyl groups, i.e., these structures are branched and not linear.

With respect to the moieties represented by subscripts m, i and j, it is to be understood that when subscript i is 0, subscript j is also 0; when subscript i is an integer greater than 0, subscript j is also an integer greater than 0; and when subscript i is an integer greater than 0, m is also an integer greater than 0. Said differently, when the group represented by subscript i is present, the group represented by subscript j is also present. The inverse is also true, i.e., when the group represented by subscript i is not present, the group represented by subscript j is also not present. In addition, when i is an integer greater than 0, the group represented by subscript m is present, and m is also an integer greater than 0. In certain embodiments, subscripts m and i are each 1. Typically, the subscript i does not exceed 1, although the subscript m may be an integer greater than 1 such that siloxane bonds (i.e., Si—O bonds) are present within the group represented by subscript i.

The polyfluoropolyether silane of the surface treatment composition is subject to the proviso that when Y is F; Z is —$(CF_2)$—; a is an integer from 1 to 3; and subscripts c, d, f and i are 0; fluorine-containing compounds represented by the general formula (B) are present in the surface treatment composition in an amount of at least 25 mol %, typically from 25 to 50 mol %, based on the total amount of the surface treatment composition: F—$(CF_2)_a$—$(OC_3F_6)_b$—$(OC_2F_4)_e$—$(OCF_2)_g$—F (B). Typically, such fluorine-containing compounds, i.e., the fluorine-containing compounds represented by general formula (B), are provided along with the perfluoropolyether-containing compound utilized to produce the surface treatment composition, as described in greater detail below.

Typically, fluorine-containing compounds of the general formula (C) below are present in the surface treatment composition in an amount of less than 40, alternatively less than 30, alternatively less than 25 mol %, based on the total amount of the surface treatment composition: Y'—$Z_a$—$[(OC_3F_6)_b$—$(OCF(CF_3)CF_2)_c$—$(OCF_2CF(CF_3))_d$—$(OC_2F_4)_e$—$(CF(CF_3))_f$—$(OCF_2)_g]$—$(CH_2)_h$—X—$(C_nH_{2n'})$—$CR^5$=$CR^5$—$CH_3$ (C).

In general formula (C) above, Y' is selected from F and $CH_3$—$CR^5$=$CR^5$—$(C_nH_{2n'})$—X—$(CH_2)_h$—; n' is an integer independently selected from 0 to 17; $R^5$ is independently selected from a hydrogen atom and a methyl group; and Z, a, b, c, d, e, f, g, h and X are as defined above. It is to be appreciated that like in the polyfluoropolyether silane, the groups represented by subscripts b-g, i.e., the groups within the square brackets in general formula (C), may be present in any order within the fluorine-containing compounds of general formula (C), including a different order as that which is represented in general formula (A) above and throughout this description. Moreover, these groups may be present in randomized or block form. As described in greater detail below, the fluorine-containing compounds represented by general formula (C) are undesirable isomers which are formed in situ when producing the polyfluoropolyether silane and the surface treatment composition. As such, it is advantageous to minimize the mol % of these isomers, i.e., the fluorine-containing compounds represented by general formula (C), in the surface treatment composition for reasons described below with respect to the method of producing the surface treatment composition.

The hydrolysable group represented by X' in general formula (A) of the polyfluoropolyether silane is independently selected from a halide group, an alkoxy (—$OR^2$) group, an alkylamino (—$NHR^2$ or —$NR^2R^3$) group, a carboxy (—OOC—$R^2$) group, an alkyliminoxy (—O—N=$CR^2R^3$) group, an alkenyloxy (O—C(=$CR^2R^3$)$R^4$) group, or an N-alkylamido (—$NR^2COR^3$) group, wherein $R^2$, $R^3$ and $R^4$ are each independently selected from H and a hydrocarbon having from 1 to 22 carbon atoms. When $R^2$, $R^3$ and $R^4$ are independently hydrocarbon groups having from 1 to 22 carbon atoms, $R^2$, $R^3$ and $R^4$ may be linear, branched, or cyclic. In addition, $R^2$, $R^3$ and $R^4$ may independently include heteroatoms within the hydrocarbon group, and may be substituted or unsubstituted. In certain embodiments, the hydrolysable group represented by X' in general formula (A) of the polyfluoropolyether silane is independently selected from an alkoxy (—$OR^2$) group and an alkylamino (—$NHR^2$ or —$NR^2R^3$) group. When the hydrolysable group represented by X' in general formula (A) of the polyfluoropolyether silane is an alkylamino group, $R^2$ and $R^3$ optionally can form a cyclic amine in the alkylamino group.

While not limited to such embodiments, exemplary embodiments of particular species of the polyfluoropolyether silane of the surface treatment composition are described in detail below. Typically in these embodiments, z is 0 such that polyfluoropolyether silane includes three hydrolysable groups represented by X'. However, it is to be appreciated that, as described above, z can be an integer other than 0 (e.g.

1 or 2) such that these particular polyfluoropolyether silanes include fewer than three hydrolysable groups.

In certain embodiments, Y in general formula (A) of the polyfluoropolyether silane of the surface treatment composition is F. Typically, when Y in general formula (A) of the polyfluoropolyether silane of the surface treatment composition is F, subscripts c, d and g in general formula (A) of the polyfluoropolyether silane are 0. As such, in these embodiments, when the groups represented by subscripts c, d and g are absent, the polyfluoropolyether silane has the general formula $Y-Z_a-[(OC_3F_6)_b-(OC_2F_4)_e-(CF(CF_3))_f]-(CH_2)_h-X-(C_nH_{2n})-((SiR_2-O)_m-SiR_2)_i-(C_jH_{2j})-Si-(X')_{3-z}(R^1)_z$.

In one embodiment in which Y in general formula (A) of the polyfluoropolyether silane of the surface treatment composition is F, as introduced above, Z in general formula (A) is $-(CF_2)-$, subscripts c, d, f and g in general formula (A) of the polyfluoropolyether silane are 0 and subscripts b, e, h and n in general formula (A) of the polyfluoropolyether silane are each independently an integer greater than 0. As but one example of this embodiment, subscript a is 3, subscript b is at least 1, subscript e is 1, subscript h is 1, X is an oxygen atom, subscript n is 3, and subscripts m, i and j are each 0. In this one example, the polyfluoropolyether silane has the following general formula: $CF_3-CF_2-CF_2-(O-CF_2-CF_2-CF_2)_b-O-CF_2-CF_2-CH_2-O-CH_2-CH_2-CH_2-Si-(X')_{3-z}(R^1)_z$. Thus, when the hydrolysable groups represented by X' are all alkoxy groups, e.g. methoxy groups, this particular polyfluoropolyether silane has the following general formula: $CF_3-CF_2-CF_2-(O-CF_2-CF_2-CF_2)_b-O-CF_2-CF_2-CH_2-O-CH_2-CH_2-CH_2-Si-(OCH_3)_3$. Alternatively, when the hydrolysable groups represented by X' are all alkylamino groups, e.g. $N(CH_3)_2$ groups, this particular polyfluoropolyether silane has the following general formula: $CF_3-CF_2-CF_2-(O-CF_2-CF_2-CF_2)_b-O-CF_2-CF_2-CH_2-O-CH_2-CH_2-CH_2-Si-(N(CH_3)_2)_3$.

In another embodiment in which Y in general formula (A) of the polyfluoropolyether silane of the surface treatment composition is F and Z in general formula (A) is $-(CF_2)-$, as described above, subscripts c, d, f and g in general formula (A) of the polyfluoropolyether silane are 0 and subscripts b, e, h, n, m, i and j in general formula (A) of the polyfluoropolyether silane are each independently an integer greater than 0. As but one example of this embodiment, subscript a is 3, subscript b is at least 1, subscript e is 1, subscript h is 1, X is an oxygen atom, subscript n is 3, subscript m and i are each 1, and subscript j is 2. In this one example, the polyfluoropolyether silane has the following general formula: $CF_3-CF_2-CF_2-(O-CF_2-CF_2-CF_2)_b-O-CF_2-CF_2-CH_2-O-CH_2-CH_2-CH_2-Si(CH_3)_2-O-Si(CH_3)_2-CH_2-CH_2-Si-(X')_{3-z}(R^1)_z$. Thus, when the hydrolysable groups represented by X' are all alkoxy groups, e.g. methoxy groups, this particular polyfluoropolyether silane has the following general formula: $CF_3-CF_2-CF_2-(O-CF_2-CF_2-CF_2)_b-O-CF_2-CF_2-CH_2-O-CH_2-CH_2-CH_2-Si(CH_3)_2-O-Si(CH_3)_2-CH_2-CH_2-Si(OCH_3)_3$.

In another embodiment in which Y in general formula (A) of the polyfluoropolyether silane of the surface treatment composition is F, as introduced above, Z in general formula (A) is $-(CF(CF_3)CF_2O)-$. In this embodiment, subscripts b, c, d, e and g in general formula (A) of the polyfluoropolyether silane are 0, and subscripts f, h and n in general formula (A) of the polyfluoropolyether silane are each independently an integer greater than 0. As but one example of this embodiment, subscripts b, c, d, e and g in general formula (A) of the polyfluoropolyether silane are 0, subscript a is at least 1, subscript f is 1, subscript h is 1, X is an oxygen atom, subscript n is 3, and subscripts i, m and j are each 0. In this one example, the polyfluoropolyether silane has the following general formula: $F-(CF(CF_3)-CF_2-O)_a-CF(CF_3)-CH_2-O-CH_2-CH_2-CH_2-Si-(X')_{3-z}(R^1)_z$. Thus, when the hydrolysable groups represented by X' are all alkoxy groups, e.g. methoxy groups, this particular polyfluoropolyether silane has the following general formula: $F-(CF(CF_3)-CF_2-O)_a-CF(CF_3)-CH_2-O-CH_2-CH_2-CH_2-Si-(OCH_3)_3$. Alternatively, when the hydrolysable groups represented by X' are all alkylamino groups, e.g. $N(CH_3)_2$ groups, this particular polyfluoropolyether silane has the following general formula: $F-(CF(CF_3)-CF_2-O)_a-CF(CF_3)-CH_2-O-CH_2-CH_2-CH_2-Si-(N(CH_3)_2)_3$.

In another embodiment in which Y in general formula (A) of the polyfluoropolyether silane of the surface treatment composition is F and Z in general formula (A) is $-(CF(CF_3)CF_2O)-$, as introduced immediately above, subscripts b, c, d, e and g in general formula (A) of the polyfluoropolyether silane are 0, subscript a is at least 1, subscript f is 1, subscript h is 1, X is an oxygen atom, subscript n is 3, subscript m and i are each 1, and subscript j is 2. In this one example, the polyfluoropolyether silane has the following general formula: $F-(CF(CF_3)CF_2O)_a-CF(CF_3)-CH_2-O-CH_2-CH_2-CH_2-Si(CH_3)_2-O-Si(CH_3)_2-CH_2-CH_2-Si-(X')_{3-z}(R^1)_z$. Thus, when the hydrolysable groups represented by X' are all alkoxy groups, e.g. methoxy groups, this particular polyfluoropolyether silane has the following general formula: $F-(CF(CF_3)CF_2O)_a-CF(CF_3)-CH_2-O-CH_2-CH_2-Si(CH_3)_2-O-Si(CH_3)_2-CH_2-CH_2-Si(OCH_3)_3$.

In other embodiments, Y in general formula (A) of the polyfluoropolyether silane is $Si-(X')_{3-z}(R^1)_z(C_jH_{2j})-((SiR_2-O)_m-SiR_2)_i-(C_nH_{2n})-X-(CH_2)_h-$. Typically, when Y in general formula (A) of the polyfluoropolyether silane of the surface treatment composition is $Si-(X')_{3-z}(R^1)_z(C_jH_{2j})-((SiR_2-O)_m-SiR_2)_i-(C_nH_{2n})-X-(CH_2)_h-$, subscripts b, c and f in general formula (A) of the polyfluoropolyether silane are 0. As such, in these embodiments, when the groups represented by subscripts b, c and f are absent, the polyfluoropolyether silane has the following general formula: $Y-Z_a-[(OCF_2CF(CF_3))_d-(OC_2F_4)_e-(OCF_2)_g]-(CH_2)_h-X-(C_nH_{2n})-((SiR_2-O)_m-SiR_2)_i-(C_jH_{2j})-Si-(X')_{3-z}(R^1)_z$.

In one embodiment in which Y in general formula (A) of the polyfluoropolyether silane of the surface treatment composition is $Si-(X')_{3-z}(R^1)_z(C_jH_{2j})-((SiR_2-O)_m-SiR_2)_i-(C_nH_{2n})-X-(CH_2)_h-$, as introduced immediately above, Z is $-(CF_2)-$, X is an oxygen atom, subscripts b, c, d and f in general formula (A) of the polyfluoropolyether silane are 0, and subscripts e and g in general formula (A) of the polyfluoropolyether silane are each independently an integer greater than 0. As but one example of this embodiment, Z is $-(CF_2)-$, X is an oxygen atom, subscripts b, c, d, f, m, i and j in general formula (A) of the polyfluoropolyether silane are 0, subscript e is at least 1, subscript g is at least 1, subscript h is 1, X is an oxygen atom, and n is 3. In this one example, the polyfluoropolyether silane has the following general formula: $(R^1)_z(X')_{3-z}Si-CH_2-CH_2-CH_2-O-CH_2-CF_2-(OCF_2CF_2)_e-(OCF_2)_g-CH_2-O-CH_2-CH_2-CH_2-Si-(X')_{3-z}(R^1)_z$. Thus, when the hydrolysable groups represented by X' are all alkoxy groups, e.g. methoxy groups, this particular polyfluoropolyether silane has the following general formula: $(CH_3O)_3Si-CH_2-CH_2-CH_2-O-CH_2-CF_2-(OCF_2CF_2)_e-(OCF_2)_g-CH_2-O-CH_2-CH_2-CH_2-Si-(OCH_3)_3$. Alternatively, when the hydrolysable groups represented by X' are all alkylamino groups, e.g. $N(CH_3)_2$ groups, this particular polyfluoropolyether silane has the following general formula: $((CH_3)_2 N)_3Si—CH_2—CH_2—CH_2—O—CH_2—CF_2—(OCF_2 CF_2)_e—(OCF_2)_g—CH_2—O—CH_2—CH_2—CH_2—Si—(N(CH_3)_2)_3$.

Alternatively, in another embodiment in which Y in general formula (A) of the polyfluoropolyether silane of the surface treatment composition is $Si—(X')_{3-z}(R^1)_z(C_jH_{2j})—((SiR_2—O)_m—SiR_2)_i—(C_nH_{2n})—X—(CH_2)_h—$, as introduced above, Z is $—(CF_2)—$, X is an oxygen atom, subscripts b, c, e and f in general formula (A) of the polyfluoropolyether silane are 0, and subscripts d and g in general formula (A) of the polyfluoropolyether silane are each independently an integer greater than 0.

The surface treatment composition of the present invention may contain a liquid medium such as an organic solvent. The concentration of the polyfluoropolyether silane represented by general formula (A) and the fluorine-containing compounds represented by general formulas (B) and (C) is preferably 0.001 to 80, alternatively 0.1 to 60, % by weight based on the total weight of the surface treatment composition. The organic solvent may be various solvents which preferably dissolve the surface treatment composition provided that the organic solvent does not react with the surface treatment composition. Examples of the organic solvent include a fluorine-containing solvent such as a fluorine-containing alkane, a fluorine-containing haloalkane, a fluorine-containing aromatic and/or a fluorine-containing ether (for example, hydrofluoroether (HFE)).

Optional catalysts can be used, if needed, to promote surface modification by the surface treatment composition of the present invention. These catalysts promote the reaction between the hydrolysable groups of the polyfluoropolyether silane and the surface of the article. These catalysts can be used alone or as a combination of two or more species to form the surface modifier of the present invention. Examples of suitable catalytic compounds include acids, bases, metal salts of organic acids such as dibutyl tin dioctoate, iron stearate, lead octoate and others, titanate esters such as tetraisopropyl titanate, tetrabutyl titanate, chelate compounds such as acetylacetonato titanium and the like. The optional catalyst are typically utilized in an amount of from 0 to 5, alternatively 0.01 to 2, parts by weight, based on 100 parts by weight of the surface treatment composition.

The surface treatment composition may additionally include any suitable other component(s) such as a coupling agent, an antistatic agent, an ultraviolet absorber, a plasticizer, a leveling agent, a pigment, a catalyst and so on.

As set forth above, the present invention also provides a method for producing the surface treatment composition comprising a polyfluoropolyether silane. In certain embodiments, the polyfluoropolyether silane produced via the method of the present invention is the polyfluoropolyether silane illustrated by general formula (A) above. However, it is to be appreciated that the polyfluoropolyether silane produced via the method of the present invention may have a structure different than the structure of the polyfluoropolyether silane illustrated by general formula (A) dependent upon the reactants utilized in the method.

When the polyfluoropolyether silane produced via the method has the following general formula (G) $Y—Z'_a—[(OC_3F_6)_b—(OC_2F_4)_e—(OCF_2)_g]—(CH_2)_h—X—(C_nH_{2n})—Si—(X')_{3-z}(R^1)_z$ (G); wherein Z' is $—(CF_2)—$; a' is an integer from 1 to 3; b, e, and g are integers each independently selected from 0 to 200; h and n are integers each independently selected from 0 to 20; X is a bivalent organic group or an oxygen atom; z is an integer independently selected from 0 to 2; X' is an independently selected hydrolysable group; $R^1$ is an independently selected hydrocarbon group having from 1 to 22 carbon atoms which is free of aliphatic unsaturation; and Y is F; fluorine-containing compounds represented by the general formula (B) below are present in the surface treatment composition in an amount of at least 25 mol % based on the total amount of the surface treatment composition: $F—(CF_2)_a—(OC_3F_6)_b—(OC_2F_4)_e—(OCF_2)_g—F$ (B). It is to be appreciated that in this instance, i.e., when the polyfluoropolyether silane has the general formula (G) above, subscript a in general formula (B) is from 1 to 3, and subscripts b, e, and g are as defined above.

The method comprises the step of providing a perfluoropolyether-containing compound having at least one aliphatically unsaturated group. The method also comprises the step of providing a hydrosilane compound. In addition, the method comprises the step of providing a hydrosilylation catalyst. The method further comprises the step of providing an isomer reducing agent. The method also comprises the step of reacting the perfluoropolyether-containing compound and the hydrosilane compound in the presence of the hydrosilylation catalyst and the isomer reducing agent, thereby producing the polyfluoropolyether silane and the surface treatment composition. Each of these method steps is described in greater detail below.

As introduced above, the method includes the step of providing a perfluoropolyether-containing compound having at least one aliphatically unsaturated group. In certain embodiments, the perfluoropolyether-containing compound having at least one aliphatically unsaturated group has the following general formula (D): $Y'—Z_a—[(OC_3F_6)_b—(OCF(CF_3)CF_2)_c—(OCF_2CF(CF_3))_d—(OC_2F_4)_e—(CF(CF_3))_f—(OCF_2)_g]—(CH_2)_h—X—(C_{n''}H_{2n''})—CR^5=CR^5H$. In general formula (D), Y' is selected from F and $CR^5H=CR^5—(C_{n''}H_{2n''})—X—(CH_2)_h—$; n'' is an integer independently selected from 0 to 16; $R^5$ is independently selected from a hydrogen atom and a methyl group; and Z, a, b, c, d, e, f, g, h and X are as defined above. It is to be appreciated that the group represented by subscript n'', i.e., the $(C_{n''}H_{2n''})$ group, may also be independently linear or branched. For example, when n'' is 3, these groups may independently have the structure $—CH_2—CH_2—CH_2—$, $—CH(CH_3)—CH_2—$, or $—CH_2—CH(CH_3)—$, wherein the latter two structures have pendent alkyl groups, i.e., these structures are branched and not linear. It is to be appreciated that the groups represented by subscripts b-g, i.e., the groups within the square brackets in general formula (D), may be present in any order within the perfluoropolyether-containing compound, including a different order as that which is represented in general formula (A) above and throughout this description.

As illustrated in general formula (D), the at least one aliphatically unsaturated group is typically an ethylenically unsaturated group. Typically, the ethylenically unsaturated group is a terminal group in the perfluoropolyether-containing compound. However, it is to be appreciated that the aliphatically unsaturated group can also be pending from the backbone of the perfluoropolyether-containing compound. In addition, as illustrated above in general formula (D), the perfluoropolyether-containing compound may be monofunctional, i.e., may contain one aliphatically unsaturated group, or may be difunctional, i.e., may include two aliphatically unsaturated groups. When the perfluoropolyether-containing compound is difunctional, the aliphatically unsaturated groups are typically located at the terminal ends of the perfluoropolyether-containing compound.

The method also comprises the step of providing a hydrosilane compound. In certain embodiments, the hydrosilane compound has the following general formula (E) H—Si(X')$_{3-z}$(R$^1$)$_z$ where X', R$^1$ and z are as defined above. Alternatively, in other embodiments, the hydrosilane compound comprises a hydrosiloxane. In embodiments in which the hydrosilane compound comprises the hydrosiloxane, the hydrosiloxane typically has the following general formula (F) H—((SiR$_2$—O)$_m$—SiR$_2$)$_i$—(C$_j$H$_{2j}$)—Si—(X')$_{3-z}$(R$^1$)$_z$ where R, m, i, j, X', z and R$^1$ are as defined above. Typically, the hydrosilane compound comprises the hydrosiloxane when the subscript i in general formula (A) is at least 1.

In certain embodiments, the hydrolysable group represented by X' in the general formula (E) above is independently selected from halogen atoms. In these embodiments, z is typically zero such that the hydrosilane has three halogen atoms bonded thereto. As one example, the hydrosilane may be trichlorosilane, which is commercially available from many suppliers.

The hydrosilylation catalyst typically comprises a catalytic Group VIII transition metal. For example, the hydrosilylation catalyst typically comprises platinum or rhodium. When the hydrosilylation catalyst comprises platinum, the hydrosilylation catalyst is typically provided as chloroplatinic acid or as a platinum complex with 1,3-divinyl-1,1,3,3-tetramethyldisiloxane or rhodium as tris-(triphenylphosphine)Rh$^I$Cl. However, it is to be appreciated that other hydrosilylation catalysts may be utilized in the method of the present invention without departing form the scope thereof.

When the hydrosilylation catalyst comprises the platinum complex, the hydrosilylation catalyst is typically utilized in an amount such that the platinum is supplied in an amount of from 0.001-100, alternatively from 0.001-50, alternatively from 0.01-10, mmol, based on 1 mole of the perfluoropolyether-containing compound.

As set forth above, the method also includes the step of providing an isomer reducing agent. In certain embodiments, the isomer reducing agent comprises a carboxylic acid compound. The carboxylic acid compound may comprise (a) carboxylic acid, (b) an anhydride of a carboxylic acid, (c) a silylated carboxylic acid, and/or (d) a substance that will produce the above-mentioned carboxylic acid compounds (i.e., (a), (b), and/or (c)) through a reaction or decomposition in the reaction of the method. It is to be appreciated that a mixture of one or more of these carboxylic acid compounds may be utilized as the isomer reducing agent. For example, a silylated carboxylic acid may be utilized in combination with an anhydride of a carboxylic acid as the isomer reducing agent. In addition, a mixture within one or more types of carboxylic acid compounds may be utilized as the isomer reducing agent. For example, two different silylated carboxylic acids may be utilized in concert, or two silylated carboxylic acids may be utilized in concert with an anhydride of a carboxylic acid.

When the isomer reducing agent comprises (a) carboxylic acid, any carboxylic acid having carboxyl groups may be utilized. Suitable examples of carboxylic acids include saturated carboxylic acids, unsaturated carboxylic acids, monocarboxylic acids, and dicarboxylic acids. A saturated or unsaturated aliphatic hydrocarbon group, aromatic hydrocarbon group, halogenated hydrocarbon group, hydrogen atom, or the like is usually selected as the portion other than the carboxyl groups in these carboxylic acids. Specific examples of suitable carboxylic acids include saturated monocarboxylic acids such as formic acid, acetic acid, propionic acid, n-butyric acid, isobutyric acid, hexanoic acid, cyclohexanoic acid, lauric acid, and stearic acid; saturated dicarboxylic acids such as oxalic acid and adipic acid; aromatic carboxylic acids such as benzoic acid and para-phthalic acid; carboxylic acids in which the hydrogen atoms of the hydrocarbon groups of these carboxylic acids have been substituted with a halogen atom or an organosilyl group, such as chloroacetic acid, dichloroacetic acid, trifluoroacetic acid, para-chlorobenzoic acid, and trimethylsilylacetic acid; unsaturated fatty acids such as acrylic acid, methacrylic acid, and oleic acid; and compounds having hydroxy groups, carbonyl groups, or amino groups in addition to carboxyl groups, namely, hydroxy acids such as lactic acid, keto acids such as acetoacetic acid, aldehyde acids such as glyoxylic acid, and amino acids such as glutamic acid.

When the isomer reducing agent comprises (b) anhydrides of carboxylic acids, suitable examples of anhydrides of carboxylic acids include acetic anhydride, propionic anhydride, and benzoic anhydride. These anhydrides of carboxylic acids may be obtained via a reaction or decomposition in the reaction system include acetyl chloride, butyryl chloride, benzoyl chloride, and other carboxylic acid halides, carboxylic acid metal salts such as zinc acetate and thallium acetate, and carboxylic esters that are decomposed by light or heat, such as (2-nitrobenzyl)propionate.

In embodiments where the isomer reducing agent comprises (c) a silylated carboxylic acid, suitable examples of silylated carboxylic acids are trialkylsilylated carboxylic acids, such as trimethylsilyl formate, trimethylsilyl acetate, triethylsilyl propionate, trimethylsilyl benzoate, and trimethylsilyl trifluoroacetate; and di-, tri-, or tetracarboxysilylates, such as dimethyldiacetoxysilane, diphenyldiacetoxysilane, methyltriacetoxysilane, ethyltriacetoxysilane, vinyltriacetoxysilane, di-t-butoxydiacetoxysilane, and silicon tetrabenzoate.

The isomer reducing agent is typically utilized in an amount of from 0.001 to 20, alternatively from 0.01 to 5, alternatively from 0.01 to 1 weight percent, based on the total amount of the perfluoropolyether-containing compound having at least one aliphatically unsaturated group utilized. Examples of a commercially available silylated carboxylic acid suitable as the isomer reducing agent are DOW CORNING® ETS 900 or XIAMETER® OFS-1579 Silane, available from Dow Corning Corporation of Midland, Mich.

As set forth above, the method comprises the step of reacting the perfluoropolyether-containing compound and the hydrosilane compound in the presence of the hydrosilylation catalyst and the isomer reducing agent. The hydrosilylation catalyst can be added all at once or incrementally over time. Alternatively, the hydrosilylation catalyst can be added continuously. Typically, the hydrosilylation catalyst is added to a reaction mixture of the perfluoropolyether-containing compound and the hydrosilane compound incrementally over time. It is to be appreciated that increments of time between the addition of the hydrosilylation catalyst to the reaction mixture of the perfluoropolyether-containing compound and the hydrosilane compound can vary and depend on a number of factors including, but not limited to, the time necessary for the reaction to complete, the relative amounts of the perfluoropolyether-containing compound and the particular hydrosilane compound, etc.

As readily understood by one of skill in the art, the perfluoropolyether-containing compound and the hydrosilane compound undergo a hydrosilylation reaction in the presence of the hydrosilylation catalyst and the isomer reducing agent. It is to be appreciated that the reaction conditions, including reaction steps and components utilized in the hydrosilylation reaction, are typically selected based on the desired hydrolysable groups X' in the polyfluoropolyether silane represented by general formula (A), as recognized by one of skill in the art. It is also readily understood by one of skill in the art, that one or more of hydrolysable group X' in the polyfluoropolyether silane represented by general formula (A) can be independently exchanged with a different hydrolysable group that may be more preferred. An example would be the reaction of a chlorinated polyfluoropolyether silane with an excess of an alkyl amine resulting in a polyfluoropolyether silane with alkyl amine hydrolysable groups.

The hydrosilylation reaction between the perfluoropolyether-containing compound and the hydrosilane is typically carried out by reacting for an appropriate time interval and temperature with an excess of silicon hydride to drive the reaction to completion. For example, the molar ratio of the perfluoropolyether-containing compound to the hydrosilane is typically 1:1 to 1:5, alternatively from 1:1.2 to 1:3. It is to be appreciated that solvent may be added to facilitate mixing. Various instrumental methods, such as Nuclear Magnetic Resonance (NMR) or Infrared (IR) spectroscopy, may be relied upon to monitor reaction progress. Any excess of silicon hydride can easily be removed from the reaction product by vacuum distillation.

During the reaction between the perfluoropolyether-containing compound and the hydrosilane compound, the perfluoropolyether-containing compound readily isomerizes to an isomer represented by the following general formula (C): $Y'-Z_a-[(OC_3F_6)_b-(OCF(CF_3)CF_2)_c-(OCF_2CF(CF_3))_d-(OC_2F_4)_e-(CF(CF_3))_f-(OCF_2)_g]-(CH_2)_h-X-(C_nH_{2n})-CR^5=CR^5-CH_3$ where the subscripts, groups, and substituents are as defined above. Notably, the perfluoropolyether-containing compound generally includes at least one ethylenically unsaturated group at one or both terminal ends of the perfluoropolyether-containing compound. However, as illustrated in general formula (C), the isomer produced from the perfluoropolyether-containing compound during the hydrosilylation compound does not include an ethylenically unsaturated group at its terminal end(s). Rather, the isomer illustrated by general formula (C) includes an ethylenically unsaturated group within the backbone of the isomer itself, and the terminal ends are typically univalent alkyl groups. Notably, the reaction between the perfluoropolyether-containing compound and the hydrosilane compound, when conducted in the absence of the isomer reducing agent, results in the isomer represented by general formula (C) being present in the resultant surface treatment composition in an amount of more than 40, alternatively more than 50, alternatively more than 60 mole percent based on the total amount of the surface treatment composition. Because of the location of the ethylenically unsaturated group of the isomer, the isomer does not readily react with the hydrosilane such that the isomer remains in the surface treatment composition after the polyfluoropolyether silane and the surface treatment composition are produced. The isomer undesirably impacts the physical properties of the surface treatment composition, such as durability.

However, when the perfluoropolyether-containing compound and the hydrosilane are reacted in the presence of the isomer reducing agent, the amount of the isomer produced is significantly reduced such that the surface treatment composition comprises a greater amount of the polyfluoropolyether silane, which is desirable. In particular, when the perfluoropolyether-containing compound and the hydrosilane are reacted in the presence of the isomer reducing agent, the isomer represented by general formula (C) above is typically present in an amount less than 40, alternatively less than 30, alternatively less than 25 mole percent based on the total amount of the surface treatment composition.

As set forth above, the present invention further provides a surface-treated article. The surface treated article comprises an article presenting a surface. A layer is deposited on the surface of the article. The layer is formed from the surface treatment composition of the present invention.

The article may be any article. However, because of the excellent physical properties obtained from the surface treatment composition of the present invention, the article is typically an electronic article, an optical article, consumer appliances and components, automotive bodies and components, etc. Most typically, the article is an article for which it is desirable to reduce stains and/or smudges resulting from fingerprints or skin oils.

Examples of electronic articles typically include those having electronic displays, such as LCD displays, LED displays, OLED displays, plasma displays, etc. These electronic displays are often utilized in various electronic devices, such as computer monitors, televisions, smart phones, GPS units, music players, remote controls, portable readers, etc. Exemplary examples of electronic articles include those having interactive touch-screen displays or other components which are often in contact with the skin and which oftentimes display stains and/or smudges.

As introduced above, the article may also be a metal article, such as consumer appliances and components. For example, the article may be a dishwasher, a stove, a microwave, a refrigerator, a freezer, etc. In these embodiments, the consumer appliances and components are those having a glossy metal appearance, such as stainless steel, brushed nickel, etc.

Alternatively, the article may be an automotive body or component. For example, the surface treatment composition may be applied directly on a top coat of an automobile body to form the layer, which imparts the automobile body with a glossy appearance, which is aesthetically pleasing and resists stains, such as dirt, etc., as well as smudges from fingerprints.

Examples of suitable optical articles include inorganic materials, such as glass plates, glass plates comprising an inorganic layer, ceramics, and the like. Additional examples of suitable optical articles include organic materials, such as transparent plastic materials and transparent plastic materials comprising an inorganic layer, etc. Specific examples of optical articles include antireflective films, optical filters, optical lenses, eyeglass lenses, beam splitters, prisms, mirrors, etc.

Examples of inorganic materials include glass plates. Examples of inorganic compounds for forming glass plates comprising an inorganic layer include metal oxides (silicon oxides, such as silicon dioxide, silicon monoxide, etc.), magnesium oxide, titanium oxide, tin oxide, zirconium oxide, sodium oxide, antimony oxide, indium oxide, bismuth oxide, yttrium oxide, cerium oxide, zinc oxide, ITO (indium tin oxide) and the like.

The inorganic layer or inorganic material comprising such an inorganic compound may be single- or multi-layered. The inorganic layer acts as an antireflective layer, and can be formed by known methods such as wet coating, PVD (physical vapor deposition), CVD (chemical vapor deposition), and like methods. Examples of wet coating methods include dip coating, spin coating, flow coating, spray coating, roll coating, gravure coating, die coating, and like methods. Examples of PVD methods include vacuum evaporation, reactive deposition, ion beam assisted deposition, sputtering, ion plating, and like methods.

Among organic materials, examples of transparent plastic materials include materials comprising various organic polymers. From the view point of transparency, refractive index, dispersibility and like optical properties, and various other properties such as shock resistance, heat resistance and durability, materials used as optical members usually comprise polyolefins (polyethylene, polypropylene, etc.), polyesters (polyethylene terephthalate, polyethylene naphthalate, etc.), polyamides (nylon 6, nylon 66, etc.), polystyrene, polyvinyl chloride, polyimides, polyvinyl alcohol, ethylene vinyl alcohol, acrylics, celluloses (triacetylcellulose, diacetylcellulose, cellophane, etc.), or copolymers of such organic polymers. It is to be appreciated that these materials may be utilized in ophthalmic elements. Non-limiting examples of ophthalmic elements include corrective and non-corrective lenses, including single vision or multi-vision lenses like bifocal, trifocal and progressive lenses, which may be either segmented or non-segmented, as well as other elements used to correct, protect, or enhance vision, including without limitation contact lenses, intra-ocular lenses, magnifying lenses and protective lenses or visors. Preferred material for ophthalmic elements comprises one or more polymers selected from polycarbonates, polyamides, polyimides, polysulfones, polyethylene terephthalate and polycarbonate copolymers, polyolefins, especially polynorbornenes, diethylene glycol-bis(allyl carbonate) polymers—known as CR39—and copolymers, (meth)acrylic polymers and copolymers, especially (meth)acrylic polymers and copolymers derived from bisphenol A, thio(meth)acrylic polymers and copolymers, urethane and thiourethane polymers and copolymers, epoxy polymers and copolymers, and episulfide polymers and copolymers.

In addition to such optical articles, the surface treatment composition of the invention can be applied to form the layer on other articles, such as window members for automobiles or airplanes, thus providing advanced functionality. To further improve surface hardness, it is also possible to perform surface modification by a so-called sol-gel process using a combination of the surface treatment composition and TEOS (tetraethoxysilane).

The surface treatment composition of the invention has excellent liquid repellency and thus can be applied to lithography and device formation. The layer may be formed from a wet coating method and/or a dry coating method of the surface treatment composition.

Specific examples of wet coating methods include dip coating, spin coating, flow coating, spray coating, roll coating, gravure coating, and like methods.

Specific examples of dry coating methods include vacuum evaporation, PVD, sputtering, CVD, and like methods. Specific examples of vacuum evaporation methods include resistive heating, electron beam, high-frequency heating, ion beam and like methods. Examples of CVD methods include plasma CVD, optical CVD, heat CVD, and like methods.

Notably, the method of disposing the surface treatment composition on the surface of the article to form the layer is not limited to wet or dry coating methods. For example, the layer may be formed via coating by atmospheric pressure plasma methods or vacuum evaporation methods.

When wet coating methods are utilized, diluent solvents are typically utilized in the surface treatment composition. Specific examples of these diluent solvents include perfluoroaliphatic hydrocarbons having 5 to 12 carbon atoms, such as perfluorohexane, perfluoromethylcyclohexane, and perfluoro-1,3-dimethylcyclohexane; polyfluorinated aromatic hydrocarbons such as bis(trifluoromethyl)benzene; polyfluorinated aliphatic hydrocarbons, perfluorobutyl methyl ether and like HFEs, etc. Such a solvent can be used singly or as a mixture of two or more. Wet coating methods are typically relied upon for materials having complicated shapes and/or large areas.

Once the layer is formed on the surface of the article from the surface treatment composition, the layer may further undergo heating, humidification, catalytic post treatment, photoirradiation, electron beam irradiation, etc.

Typically, the thickness of the layer formed from the surface treatment composition is from 1 to 5,000, alternatively 1 to 200, alternatively 1-20, alternatively 1 to 10, nm.

The following examples, illustrating the method of producing the polyfluoropolyether silane of the present invention, are intended to illustrate and not to limit the invention. It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

EXAMPLES

Practical Examples 1-6 and Comparative Example 1

In Practical Examples 1-6 and Comparative Example 1, one method of producing a surface treatment composition comprising a polyfluoropolyether silane is described wherein the hydrolysable groups of the polyfluoropolyether silane are alkoxy groups. As described below and illustrated in Table 1, Practical Examples 1-6 and Comparative Example 1 are identical but for the relative amount of the isomer reducing agent. Thus, for Practical Examples 1-6 and Comparative Example 1, the method described below is repeated with the exception of the presence/absence or relative amount of the isomer reducing agent.

To a 100 ml four necked flask equipped with an agitator, a digital thermometer, a reflux condenser, and a dry nitrogen purge was added 20 g (ca. 4.9 mmol) of allyloxy terminated perfluoropolyether, 1.5 g (11.1 mmol) of trichlorosilane, 10 g of reaction solvent, and an isomer reducing agent (except for in Comparative Example 1, which did not include the isomer reducing agent), to form a reaction mixture. The allyloxy terminated perfluoropolyether had the following general formula $F(CF_2CF_2CF_2O)_xCF_2CF_2CH_2OCH_2CH=CH_2$ with Mn=4110 and included fluorine-containing compounds represented by general formula (B) in an amount of 30 mole %. The amount of isomer reducing agent relative to allyloxy terminated perfluoropolyether is illustrated in Table 1. The reaction mixture was stirred at 150 rpm and heated to 60° C. 0.5 mg of a complex of platinum (4% wt. Pt) and 1,3-diethenyl-1,1,3,3-tetramethyldisiloxane was added to the reaction mixture incrementally over 4 hrs at 60° C. The reaction mixture was cooled to room temperature. The reaction solvent and residual trichlorosilane were removed by vacuum stripping. Then a mixture of trimethyl orthoformate (30 g (283 mmol)) and methanol (350 mg (11.1 mmol)) were loaded into the flask. The temperature of the flask was maintained at 65° C. to facilitate methoxylation of the chlorosilane. After 7 hrs, the reaction mixture was cooled to 30° C. Excess reagents and generated byproducts were removed by vacuum stripping. 0.1 g of dried activated carbon was added into the stripping residue and aged for 6 hours at room temperature. The activated carbon was removed by filtration and 21.0 g of filtrate was collected. The results are illustrated below in Table 1, including the relative amounts of the polyfluoropolyether silane, the isomerized perfluoropolyether compounds and the fluorine-containing compounds represented by general formula (B) (which are nonreactive).

In Practical Examples 1-6 and Comparative Example 1, the perfluoropolyether-containing compound having at least one aliphatically unsaturated group is allyloxy terminated perfluoropolyether and 30 mole % of fluorine-containing compounds represented by general formula (B) (which are nonreactive).

The hydrosilane compound is trichlorosilane.

The isomer reducing agent is a silylated carboxylic acid compound, commercially available under the trade name Dow Corning® ETS 900 from Dow Corning Corporation of Midland, Mich.

The hydrosilylation catalyst is a complex of platinum (4% wt. Pt) and 1,3-diethenyl-1,1,3,3-tetramethyldisiloxane).

The reaction solvent represented by PFX is perfluoroxylene.

The reaction solvent represented by PFH is perfluorohexane.

The reaction solvent represented by HFE is n-perfluoropropylethether.

As clearly illustrated in Table 1, Practical Examples 1-6 had a much greater yield of the particular polyfluoropolyether silane than Comparative Example 1. Not only did the surface treatment compositions of Practical Examples 1-6 have a greater yield of the polyfluoropolyether silane, but these surface treatment compositions included far less of the isomerized perfluoropolyether compound. These excellent results obtained via Practical Examples 1-6 are attributable to the isomer reducing agent, which is utilized in Practical Examples 1-6, but not utilized in Comparative Example 1. In Comparative Example 1, the surface treatment composition included almost 42 mole % of the isomerized perfluoropolyether compound (which is described above as a fluorine-containing compound represented by general formula (C)). In contrast, the surface treatment compositions of Practical Examples 1-6 included, at most, 15.7 mole % of the isomerized perfluoropolyether compound.

Practical Example 7 and Comparative Example 2

The method of producing the polyfluoropolyether silane utilized in Practical Examples 1-6 and Comparative Example 1 was repeated in Practical Example 7 and Comparative Example 2. However, in Practical Example 7 and Compara-

TABLE 1

| Example | Isomer reducing agent (ppm) | Polyfluoropolyether silane (mol %) | Isomerized perfluoropolyether compound (mol %) | Fluorine-containing compounds (mol %) | Reaction Solvent |
|---|---|---|---|---|---|
| Comparative Example 1 | 0 | 28.4 | 41.7 | 30 | PFX |
| Practical Example 1 | 100 | 54.3 | 15.7 | 30 | PFX |
| Practical Example 2 | 500 | 56.7 | 13.3 | 30 | PFX |
| Practical Example 3 | 1000 | 56.4 | 13.6 | 30 | PFH |
| Practical Example 4 | 2000 | 56.8 | 13.2 | 30 | PFH |
| Practical Example 5 | 25000 | 55.2 | 14.8 | 30 | PFH |
| Practical Example 6 | 2000 | 56.6 | 13.4 | 30 | HFE | tive Example 2, the hydrosilane compound is trimethoxysilane, rather than the trichlorosilane utilized in the method of Practical Examples 1-6 and Comparative Example 1. As such, in Practical Example 7 and Comparative Example 2, the step of methoxylating the chlorosilane is not carried out because the hydrosilane compound utilized imparts the polyfluoropolyether silane with alkoxy hydrolysable groups. In Practical Example 7, 0.2% of the isomer reducing agent was utilized relative to the total amount of the perfluoropolyether-containing compound utilized. In Comparative Example 2, no isomer reducing agent was utilized. The results obtained from Practical Example 7 and Comparative Example 2 are set forth below in Table 2.

TABLE 2

| Example | Isomer reducing agent (ppm) | Polyfluoropolyether silane (mol %) | Isomerized perfluoropolyether compound (mol %) | Fluorine-containing compounds (mol %) | Reaction Solvent |
|---|---|---|---|---|---|
| Comparative Example 2 | 0 | 27.5 | 42.5 | 30 | PFX |
| Practical Example 7 | 2000 | 53.3 | 12.7 | 30 | PFX |

As clearly illustrated in Table 2, Practical Example 7 had a much greater yield of the particular polyfluoropolyether silane than Comparative Example 2. Not only did the surface treatment composition of Practical Example 7 have a greater yield of the polyfluoropolyether silane, but this surface treatment composition included far less of the isomerized perfluoropolyether compound. These excellent results obtained via Practical Example 7 are attributable to the isomer reducing agent, which is utilized in Practical Example 7, but not utilized in Comparative Example 2. In Comparative Example 2, the surface treatment composition included 42.5 mole % of the isomerized perfluoropolyether compound (which is described above as a fluorine-containing compound represented by general formula (C)). In contrast, the surface treatment composition of Practical Example 7 included only 12.7 mole % of the isomerized perfluoropolyether compound.

Practical Example 8

The method of producing the polyfluoropolyether silane utilized in Practical Examples 1-6 and Comparative Example 1 was also repeated in Practical Example 8. However, the hydrosilylation catalyst in Practical Example 8 is Pt supported on alumina. In addition, in Practical Example 8, 0.4% of the isomer reducing agent is utilized relative to the amount of the perfluoropolyether-containing compound utilized. Once again, the polyfluoropolyether silane obtained from Practical Example 8 includes alkoxy hydrolysable groups. The results obtained from Practical Example 8 are set forth below in Table 3

As clearly evidenced above in Table 3, in Practical Example 8, the yield of the polyfluoropolyether silane in the surface treatment composition was 60.9 mole %, and the isomerized perfluoropolyether compound was only present in the surface treatment composition in an amount of 9.1 mole %.

Practical Example 9

The method of producing the polyfluoropolyether silane utilized in Practical Examples 1-6 and Comparative Example 1 was also repeated in Practical Example 9. However, the hydrosilylation catalyst in Practical Example 9 is a complex of platinum (23% wt. Pt) and 1,3-diethenyl-1,1,3,3-tetramethyldisiloxane), totaling 0.003 grams. In addition, in Practical Example 9, 0.2% of the isomer reducing agent is utilized relative to the amount of the perfluoropolyether-containing compound utilized. Following the hydrosilylation with trichlorosilane and removal of excess reagents and reaction solvent by vacuum stripping, instead of methoxylation to provide alkoxy hydrolyzable groups, the polyfluoropolyether trichlorosilane was aminated with an excess of dimethylamine. As such, the polyfluoropolyether silane produced in Practical Example 9 had tris(dimethylamino) hydrolysable groups. The amination process utilized in Practical Example 9 is described immediately below.

To a 250 ml three necked flask equipped with an agitator, a thermometer, a dry ice reflux condenser, and a dry nitrogen headspace purge was added 75 g (ca. 18 mmol) of trichlorosilyl terminated perfluoropolyether and 195 grams of perfluorohexane solvent. Anhydrous dimethylamine (commercially available from Aldrich Chemical Company of Milwaukee, Wis.) was fed into the headspace until 40.2 grams (ca. 893 mmol) had been added, which cooled the contents of the flask to 6° C. The flask was stirred with a nitrogen headspace purge and the dry ice was allowed to evaporate from the reflux condenser which allowed the reaction mixture to warm slowly to ambient temperature over 16 hours. The salt slurry was filtered to isolate the tris(dimethylamino)-functional polyfluoropolyether silane as the filtrate. Solvent was removed by vacuum stripping. The results obtained from Practical Example 9 are set forth below in Table 4

TABLE 3

| Example | Isomer reducing agent (ppm) | Polyfluoropolyether silane (mol %) | Isomerized perfluoropolyether compound (mol %) | Fluorine-containing compounds (mol %) | Reaction Solvent |
|---|---|---|---|---|---|
| Practical Example 8 | 4000 | 60.9 | 9.1 | 30 | PFX |

TABLE 4

| Example | Isomer reducing agent (ppm) | Polyfluoropolyether silane (mol %) | Isomerized perfluoropolyether compound (mol %) | Fluorine-containing compounds (mol %) | Reaction Solvent |
|---|---|---|---|---|---|
| Practical Example 9 | 2000 | 60.8 | 9.2 | 30 | PFX |

As clearly evidenced above in Table 4, in Practical Example 9, the yield of the polyfluoropolyether silane in the surface treatment composition was 60.8 mole %, and the isomerized perfluoropolyether compound was only present in the surface treatment composition in an amount of 9.2 mole %.

Evaluation of Materials

Physical properties of layers formed from certain surface treatment compositions formed above are measured. To measure the physical properties of layers formed from the surface treatment compositions of Practical Example 4 and Comparative Example 1, glass was pre-cleaned via corona discharge. A vacuum chamber at 0.14 Torr pressure containing both the glass substrate and a crucible containing the respective surface treatment composition. The crucible temperature was increased to 310° C. in 90 minutes to evaporate the surface treatment composition. After removing the coated glass substrate from the chamber, the surface was dry wiped with a fine fiber cloth.

The contact and sliding angles of layers formed from the surface treatment compositions of Practical Example 4 and Comparative Example 1 are measured via a contact angle meter commercially available under the trade name CA-DT from Kyowa Interface Science Co., Ltd. In particular, a 1 microliter droplet of water was utilized to measure contact angle and a 20 microliter droplet of water was utilized to measure sliding angle. As illustrated in Table 5 below, the initial water contact angle was measured, the glass surface was rinsed with perfluorohexane, and the contact angle was remeasured. In Table 5 below, gap refers to the difference between the two measurements and illustrates an improvement in bonding to the surface with respect to the surface treatment composition of Practical Example 4.

TABLE 5

| | Contact Angle for Water (degrees) | | |
|---|---|---|---|
| Example | Initial | Rinsed | Gap |
| Comparative Example 1 | 106.4 | 64.5 | 41.9 |
| Practical Example 4 | 102.6 | 91.1 | 11.5 |

In Table 6 below, the water sliding angle was measured as a function of increasing abrasion cycles for layers formed from the surface treatment compositions of Practical Example 4 and Comparative Example 1, respectively. These layers were formed via the physical vapor deposition method described above. The treated glass was rubbed with BEM-COT™ M-3II (commercially available from Asahi Kasei Fibers Corporation). The load was 500 g/cm$^2$.

TABLE 6

| | Sliding Angle for Water (degrees) | | | | |
|---|---|---|---|---|---|
| Example | 0 Rubbing Cycles | 100 Rubbing Cycles | 500 Rubbing Cycles | 1000 Rubbing Cycles | 5000 Rubbing Cycles |
| Comparative Example 1 | 24 | 22.3 | 19.7 | 19 | 26.7 |
| Practical Example 4 | 10.7 | 14.3 | 16.3 | 13.3 | 15.3 |

As clearly illustrated in Table 6 above, the layer formed from the surface treatment composition of Practical Example 4 had a much lower initial sliding angle than the layer formed from the surface treatment composition of Comparative Example 1. Moreover, the layer formed from the surface treatment composition of Practical Example 4 had excellent durability relative to the layer formed from the surface treatment composition of Comparative Example 1, as evidenced by the sliding angle over various rubbing cycles.

The present invention has been described herein in an illustrative manner, and it is to be understood that the terminology which has been used is intended to be in the nature of words of description rather than of limitation. Obviously, many modifications and variations of the present invention are possible in light of the above teachings. The invention can be practiced otherwise than as specifically described within the scope of the appended claims.

What is claimed is:

1. A surface treatment composition comprising a polyfluoropolyether silane having the following general formula (A):

$$Y-Z_a-([(OC_3F_6)_b-(OCF(CF_3)CF_2)_c-(OCF_2CF(CF_3))_d-(OC_2F_4)_e-(CF(CF_3))_f-(OCF_2)_g]-(CH_2)_h-X-(C_nH_{2n})-((SiR_2-O)_m-SiR_2)_i-(C_jH_{2j})-Si-(X')_{3-z}(R^1)_z \quad (A);$$

wherein Z is independently selected from —(CF$_2$)—, —(CF(CF$_3$)CF$_2$O)—, —(CF$_2$CF(CF$_3$)O)—, —(CF(CF$_3$)O)—, —(CF(CF$_3$)CF$_2$)—, —(CF$_2$CF(CF$_3$))—, and —(CF(CF$_3$))—; a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; R$^1$ is an independently selected hydrocarbon group having from 1 to 22 carbon atoms which is free of aliphatic unsaturation; and Y is selected from F and Si—(X')$_{3-z}$(R$^1$)$_z$(C$_j$H$_{2j}$)—((SiR$_2$—O)$_m$—SiR$_2$)$_i$—(C$_n$H$_{2n}$)—X—(CH$_2$)$_h$—; wherein X', z, R$^1$, j, m, i, n and h are as defined above;

provided that when subscript i is 0, subscript j is also 0; when subscript i is an integer greater than 0, subscript j is also integer greater than 0; and when subscript i is an integer greater than 0, m is also an integer greater than 0;

with the proviso that when Y is F; Z is —(CF$_2$)—; a is an integer from 1 to 3; and subscripts c, d, f and i are 0; fluorine-containing compounds represented by the general formula (B) below are present in said surface treatment composition in an amount of at least 25 mol % based on the total amount of said surface treatment composition $$F—(CF_2)_a—(OC_3F_6)_b—(OC_2F_4)_e—(OCF_2)_g—F \qquad (B);$$

and with the proviso that fluorine-containing compounds represented by the general formula (C) below are present in said surface treatment composition in an amount of less than 40 mol % based on the total amount of said surface treatment composition $$Y'—Z_a—[(OC_3F_6)_b—(OCF(CF_3)CF_2)_c—(OCF_2CF(CF_3))_d—(OC_2F_4)_e—(CF(CF_3))_f—(OCF_2)_g]—(CH_2)_h—X—(C_nH_{2n'})—CR^5{=}CR^5—CH_3 \qquad (C);$$

wherein Y' is selected from F and CH$_3$—CR$^5$=CR$^5$—(C$_n$H$_{2n'}$)—X—(CH$_2$)$_h$; n' is an integer independently selected from 0 to 17; R$^5$ is independently selected from a hydrogen atom and a methyl group; and Z, a, b, c, d, e, f, g, h and X are as defined above.

2. A surface treatment composition as set forth in claim 1 wherein said hydrolysable group represented by X' in general formula (A) of said polyfluoropolyether silane is independently selected from a halide group, an alkoxy (—OR$^2$) group, an alkylamino (—NHR$^2$ or —NR$^2$R$^3$) group, a carboxy (—OOC—R$^2$) group, an alkyliminoxy (—O—N=CR$^2$R$^3$) group, an alkenyloxy (O—C(=CR$^2$R$^3$)R$^4$) group, or an N-alkylamido (—NR$^2$COR$^3$) group, wherein R$^2$, R$^3$ and R$^4$ are each independently selected from H and a hydrocarbon having from 1 to 22 carbon atoms, and wherein R$^2$ and R$^3$ optionally can form a cyclic amine in the alkylamino group.

3. A method for producing a surface treatment composition which comprises a polyfluoropolyether silane, said method comprising the steps of:
providing a perfluoropolyether-containing compound having at least one aliphatically unsaturated group;
providing a hydrosilane compound;
providing a hydrosilylation catalyst;
providing an isomer reducing agent; and
reacting the perfluoropolyether-containing compound and the hydrosilane compound in the presence of the hydrosilylation catalyst and the isomer reducing agent, thereby producing the polyfluoropolyether silane and the surface treatment composition;
with the proviso that when the polyfluoropolyether silane has the following general formula (G), $$Y—Z'_a—[(OC_3F_6)_b—(OC_2F_4)_e—(OCF_2)_g]—(CH_2)_h—X—(C_nH_{2n})—Si—(X')_{3-z}(R^1)_z \qquad (G);$$

wherein Z' is —(CF$_2$)—; a' is an integer from 1 to 3; b, e, and g are integers each independently selected from 0 to 200; h and n are integers each independently selected from 0 to 20; X is a bivalent organic group or an oxygen atom; z is an integer independently selected from 0 to 2; X' is an independently selected hydrolysable group; R$^1$ is an independently selected hydrocarbon group having from 1 to 22 carbon atoms which is free of aliphatic unsaturation; and Y is F;
fluorine-containing compounds represented by the general formula (B) below are present in the surface treatment composition in an amount of at least 25 mol % based on the total amount of the surface treatment composition $$F—(CF_2)_a—(OC_3F_6)_b—(OC_2F_4)_e—(OCF_2)_g—F \qquad (B);$$

wherein a is from 1 to 3 in general formula (B) and b, e and g are as defined above.

4. A method as set forth in claim 3 wherein the polyfluoropolyether silane has the following general formula (A):

$$Y—Z_a—[(OC_3F_6)_b—(OCF(CF_3)CF_2)_c—(OCF_2CF(CF_3))_d—(OC_2F_4)_e—(CF(CF_3))_f—(OCF_2)_g]—(CH_2)_h—X—(C_nH_{2n})—((SiR_2—O)_m—SiR_2)_i—(C_jH_{2j})—Si—(X')_{3-z}(R^1)_z \qquad (A);$$

wherein Z is independently selected from —(CF$_2$)—, —(CF(CF$_3$)CF$_2$O)—, —(CF$_2$CF(CF$_3$)O)—, —(CF(CF$_3$)O)—, —(CF(CF$_3$)CF$_2$)—, —(CF$_2$CF(CF$_3$))—, and —(CF(CF$_3$))—; a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; R$^1$ is an independently selected hydrocarbon group having from 1 to 22 carbon atoms which is free of aliphatic unsaturation; and Y is selected from F and Si—(X')$_{3-z}$(R$^1$)$_z$(C$_j$H$_{2j}$)—((SiR$_2$—O)$_m$—SiR$_2$)$_i$—(C$_n$H$_{2n}$)—X—(CH$_2$)$_h$—; wherein X', z, R$^1$, j, m, i, n and h are as defined above;
provided that when subscript i is 0, subscript j is also 0; when subscript i is an integer greater than 0, subscript j is also an integer greater than 0; and when subscript i is an integer greater than 0, m is also an integer greater than 0;
with the proviso that when Y is F; Z is —(CF$_2$)—; a is an integer from 1 to 3; and subscripts c, d, f and i are 0; fluorine-containing compounds represented by the general formula (B) below are present in the surface treatment composition in an amount of at least 25 mol % based on the total amount of the surface treatment composition $$F—(CF_2)_a—(OC_3F_6)_b—(OC_2F_4)_e—(OCF_2)_g—F \qquad (B).$$

5. A method as set forth in claim 4 wherein the hydrolysable group represented by X' in general formula (A) of the polyfluoropolyether silane is independently selected from a halide group, an alkoxy (—OR$^2$) group, an alkylamino (—NHR$^2$ or —NR$^2$R$^3$) group, a carboxy (—OOC—R$^2$) group, an alkyliminoxy (—O—N=CR$^2$R$^3$) group, an alkenyloxy (O—C(=CR$^2$R$^3$)R$^4$) group, or an N-alkylamido (—NR$^2$COR$^3$) group, wherein R$^2$, R$^3$ and R$^4$ are each independently selected from H and a hydrocarbon having from 1 to 22 carbon atoms, and wherein R$^2$ and R$^3$ optionally can form a cyclic amine in the alkylamino group.

6. A method as set forth in claim 3 wherein the isomer reducing agent comprises a carboxylic acid compound.

7. A method as set forth in claim 3 wherein the isomer reducing agent comprises one or more silylated carboxylic acids.

8. A method as set forth in claim 3 wherein fluorine-containing compounds represented by the general formula (C) below are present in the surface treatment composition in an amount of less than 40 mol % based on the total amount of the surface treatment composition $$Y'—Z_a—[(OC_3F_6)_b—(OCF(CF_3)CF_2)_c—(OCF_2CF(CF_3))_d—(OC_2F_4)_e—(CF(CF_3))_f—(OCF_2)_g]—(CH_2)_h—X—(C_nH_{2n'})—CR^5{=}CR^5—CH_3 \qquad (C);$$

wherein Y' is selected from F and CH$_3$—CR$^5$=CR$^5$—(C$_n$H$_{2n'}$)—X—(CH$_2$)$_h$—; n' is an integer independently selected from 0 to 17; R$^5$ is independently selected from a hydrogen atom and a methyl group; and Z, a, b, c, d, e, f, g, h and X are as defined above.

9. A surface treatment composition comprising a polyfluoropolyether silane,
wherein said polyfluoropolyether silane is formed from
a perfluoropolyether-containing compound, and
a hydrosilane compound; in the presence of
a hydrosilylation catalyst, and
an isomer reducing agent;
wherein said polyfluoropolyether silane has the following general formula (A):

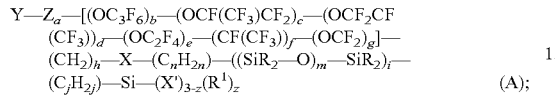

wherein Z is independently selected from $-(CF_2)-$, $-(CF(CF_3)CF_2O)-$, $-(CF_2CF(CF_3)O)-$, $-(CF(CF_3)O)-$, $-(CF(CF_3)CF_2)-$, $-(CF_2CF(CF_3))-$, and $-(CF(CF_3))-$; a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; $R^1$ is an independently selected hydrocarbon group having from 1 to 22 carbon atoms which is free of aliphatic unsaturation; and Y is selected from F and $Si-(X')_{3-z}(R^1)_z(C_jH_{2j})-((SiR_2-O)_m-SiR_2)_i-(C_nH_{2n})-X-(CH_2)_h-$; wherein X', z, $R^1$, j, m, i, n and h are as defined above;
provided that when subscript i is 0, subscript j is also 0; when subscript i is an integer greater than 0, subscript j is also an integer greater than 0; and when subscript i is an integer greater than 0, m is also an integer greater than 0;
with the proviso that when Y is F; Z is $-(CF_2)-$; a is an integer from 1 to 3; and subscripts c, d, f and i are 0; fluorine-containing compounds represented by the general formula (B) below are present in said surface treatment composition in an amount of at least 25 mol % based on the total amount of said surface treatment composition

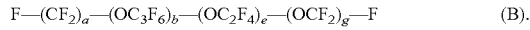

10. A surface treatment composition as set forth in claim 9 wherein said hydrolysable group represented by X' in general formula (A) of said polyfluoropolyether silane is independently selected from a halide group, an alkoxy ($-OR^2$) group, an alkylamino ($-NHR^2$ or $-NR^2R^3$) group, a carboxy ($-OOC-R^2$) group, an alkyliminoxy ($-O-N=CR^2R^3$) group, an alkenyloxy ($O-C(=CR^2R^3)R^4$) group, or an N-alkylamido ($-NR^2COR^3$) group, wherein $R^2$, $R^3$ and $R^4$ are each independently selected from H and a hydrocarbon having from 1 to 22 carbon atoms, and wherein $R^2$ and $R^3$ optionally can form a cyclic amine in the alkylamino group.

11. A surface treatment composition as set forth in claim 9 wherein the isomer reducing agent comprises a carboxylic acid compound.

12. A surface treatment composition as set forth in claim 9 wherein the isomer reducing agent comprises one or more silylated carboxylic acids.

13. A surface-treated article comprising;
an article presenting a surface; and
a layer deposited on said surface of said article;
wherein said layer is formed from a surface treatment composition which comprises a polyfluoropolyether silane;
wherein said polyfluoropolyether silane has the following general formula (A):

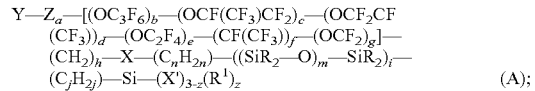

wherein Z is independently selected from $-(CF_2)-$, $-(CF(CF_3)CF_2O)-$, $-(CF_2CF(CF_3)O)-$, $-(CF(CF_3)O)-$, $-(CF(CF_3)CF_2)-$, $-(CF_2CF(CF_3))-$, and $-(CF(CF_3))-$; a is an integer from 1 to 200; b, c, d, e, f, and g are integers each independently selected from 0 to 200; h, n and j are integers each independently selected from 0 to 20; i and m are integers each independently selected from 0 to 5; X is a bivalent organic group or an oxygen atom; R is a hydrocarbon group having from 1 to 22 carbon atoms; z is an integer independently selected from 0 to 2; X' is an independently selected hydrolysable group; $R^1$ is an independently selected hydrocarbon group having from 1 to 22 carbon atoms which is free of aliphatic unsaturation; and Y is selected from F and $Si-(X')_{3-z}(R^1)_z(C_jH_{2j})-((SiR_2-O)_m-SiR_2)_i-(C_nH_{2n})-X-(CH_2)_h-$; wherein X', z, $R^1$, j, m, i, n and h are as defined above;
provided that when subscript i is 0, subscript j is also 0; when subscript i is an integer greater than 0, subscript j is also an integer greater than 0; and when subscript i is an integer greater than 0, m is also an integer greater than 0;
with the proviso that when Y is F; Z is $-(CF_2)-$; a is an integer from 1 to 3; and subscripts c, d, f and i are 0; fluorine-containing compounds represented by the general formula (B) below are present in said surface treatment composition in an amount of at least 25 mol % based on the total amount of said surface treatment composition

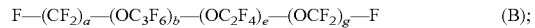

and with the proviso that fluorine-containing compounds represented by the general formula (C) below are present in said surface treatment composition in an amount of less than 40 mol % based on the total amount of said surface treatment composition

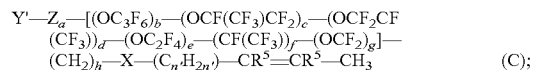

wherein Y' is selected from F and $CH_3-CR^5=CR^5-(C_nH_{2n'})-X-(CH_2)_h-$; n' is an integer independently selected from 0 to 17; $R^5$ is independently selected from a hydrogen atom and a methyl group; and Z, a, b, c, d, e, f, g, h and X are as defined above.

14. A surface-treated article as set forth in claim 13 wherein the hydrolysable group represented by X' in general formula (A) of said polyfluoropolyether silane is independently selected from a halide group, an alkoxy ($-OR^2$) group, an alkylamino ($-NHR^2$ or $-NR^2R^3$) group, a carboxy ($-OOC-R^2$) group, an alkyliminoxy ($-O-N=CR^2R^3$) group, an alkenyloxy ($O-C(=CR^2R^3)R^4$) group, or an N-alkylamido ($-NR^2COR^3$) group, wherein $R^2$, $R^3$ and $R^4$ are each independently selected from H and a hydrocarbon having from 1 to 22 carbon atoms, and wherein $R^2$ and $R^3$ optionally can form a cyclic amine in the alkylamino group.

15. A surface-treated article as set forth in claim 13 wherein said article is further defined as an electronic article.

16. A method as set forth in claim 4 wherein the isomer reducing agent comprises one or more silylated carboxylic acids.

17. A method as set forth in claim 4 wherein fluorine-containing compounds represented by the general formula (C) below are present in the surface treatment composition in an amount of less than 40 mol % based on the total amount of the surface treatment composition $$Y'-Z_a-[(OC_3F_6)_b-(OCF(CF_3)CF_2)_c-(OCF_2CF(CF_3))_d-(OC_2F_4)_e-(CF(CF_3))_f-(OCF_2)_g]-(CH_2)_h-X-(C_{n'}H_{2n'})-CR^5=CR^5-CH_3 \quad (C);$$

wherein Y' is selected from F and $CH_3-CR^5=CR^5-(C_{n'}H_{2n'})-X-(CH_2)_h-$; n' is an integer independently selected from 0 to 17; $R^5$ is independently selected from a hydrogen atom and a methyl group; and Z, a, b, c, d, e, f, g, h and X are as defined above.

* * * * *